US010828269B2

(12) United States Patent
Naito et al.

(10) Patent No.: US 10,828,269 B2
(45) Date of Patent: Nov. 10, 2020

(54) REDUCING MUSCLE ATROPHY BY ADMINISTERING ASTAXANTHIN

(71) Applicant: FUJI CHEMICAL INDUSTRIES CO., LTD., Toyama (JP)

(72) Inventors: Yuji Naito, Shiga (JP); Jiro Takahashi, Toyama (JP); Wataru Aoi, Kyoto (JP)

(73) Assignee: FUJI CHEMICAL INDUSTRIES CO., LTD., Toyama (JP)

( * ) Notice: Subject to any disclaimer, the term of this patent is extended or adjusted under 35 U.S.C. 154(b) by 343 days.

(21) Appl. No.: 14/526,880

(22) Filed: Oct. 29, 2014

(65) Prior Publication Data

US 2015/0057365 A1    Feb. 26, 2015

Related U.S. Application Data

(60) Continuation of application No. 12/155,914, filed on Jun. 11, 2008, now abandoned, and a division of application No. 11/498,725, filed on Aug. 4, 2006, now abandoned, which is a continuation of application No. PCT/JP2005/001718, filed on Feb. 4, 2005.

(30) Foreign Application Priority Data

Feb. 4, 2004  (JP) ................. 2004-028698

(51) Int. Cl.
| | |
|---|---|
| A23L 33/11 | (2016.01) |
| A61K 31/122 | (2006.01) |
| A61K 31/21 | (2006.01) |
| A23L 33/10 | (2016.01) |
| A23L 33/105 | (2016.01) |
| A23L 2/52 | (2006.01) |

(52) U.S. Cl.
CPC .............. *A61K 31/122* (2013.01); *A23L 2/52* (2013.01); *A23L 33/10* (2016.08); *A23L 33/105* (2016.08); *A61K 31/21* (2013.01); *A23V 2002/00* (2013.01)

(58) Field of Classification Search
CPC .... A23L 1/3002; A23L 33/11; A23V 2002/00
USPC ........................................................ 514/691
See application file for complete search history.

(56) References Cited

U.S. PATENT DOCUMENTS

| | | | |
|---|---|---|---|
| 5,648,334 A | 7/1997 | Davis et al. | |
| 6,245,818 B1 | 6/2001 | Lignell | |
| 6,258,855 B1 * | 7/2001 | Lorenz | A61K 9/48 514/691 |
| 6,773,708 B1 * | 8/2004 | Lignell | A61K 31/122 424/195.17 |
| 2003/0077288 A1 | 4/2003 | Goldberg et al. | |
| 2003/0078304 A1 * | 4/2003 | Andersson | A61K 31/12 514/691 |
| 2003/0206972 A1 | 11/2003 | Babish et al. | |

FOREIGN PATENT DOCUMENTS

| | | |
|---|---|---|
| EP | 1267857 | 2/2001 |
| JP | 10-327865 A | 12/1998 |
| JP | A-2001-114673 | 4/2001 |
| JP | A-2001-514215 | 9/2001 |
| JP | 2002-226368 A | 8/2002 |
| JP | 2003-265136 A | 9/2003 |
| JP | 2003-528139 A | 9/2003 |
| WO | WO 99/11251 | 3/1999 |
| WO | WO 01/72296 A1 | 10/2001 |
| WO | WO2005/074907 | 8/2005 |

OTHER PUBLICATIONS

Mondelli et al., 2001, Clinical Neurophysiology, 112, 1237-1342.*
Reid et al., 2001, Respiratory Research, 2, 269-272.*
Visser et al., 2002, Journal of Gerontology, 57A, M326-M322.*
Allen et al. Muscle Atrophy Associated With Multiple Sclerosis: A Benign Condition of the Onset of Amyotrophic Lateral Sclerosis?; Journal of Clinical Neuroscience, vol. 15, pp. 706-708. (Year: 2008).*
Andersen et al. Atrophy of Foot Muscles; Diabetes Care, vol. 27, pp. 2392-2385. (Year: 2004).*
Cuoco et al. Skeletal Muscle Wastage in Crohn'S Disease: A Pathway Shared With Heart Failure?; International Journal of Cardiology, vol. 127, pp. 219-227. (Year: 2008).*
Miro et al. Muscle Involvement in Rheumatoid Arthritis: Clinicopathological Study of 21 Symtomatic Cases; Seminars in Arthritis and Rheumatism, vol. 25, No. 6, pp. 421-428. (Year: 1996).*
Hunter et al. Activation of an Alternative NK-KAPPAB Pathway in Skeletal Muscle During Disuse Atrophy; FASEB journal, vol. 16, No. 6, pp. 529-538 (Year: 2002).*

(Continued)

*Primary Examiner* — Juliet C Switzer
*Assistant Examiner* — Paul C Martin
(74) *Attorney, Agent, or Firm* — Venable LLP; Keith G. Haddaway; Miguel A. Lopez

(57) ABSTRACT

An object of the invention is to provide a gene expression regulating agent which includes astaxanthin and/or its ester as an effective ingredient; and a food and drink having an effect of regulating gene expression which includes astaxanthin and/or its ester. Abnormal gene expression due to, for example, oxidative stress can be treated, improved, and/or prevented, and diseases caused by the abnormal gene expression can be treated, improved, and/or prevented. A gene expression regulating agent which includes astaxanthin and/or its ester as an effective ingredient; and a food and drink having an effect of regulating gene expression which includes astaxanthin and/or its ester are provided and are useful for treating, improving, and/or preventing the symptom caused by the abnormal gene expression, that is, excessive expression or suppression of expression.

7 Claims, 1 Drawing Sheet

(56) References Cited

OTHER PUBLICATIONS

Anonymous. Denervated Muscle Atrophy; Jama, vol. 72, No. 5, pp. 348-349 (Abstract only) (Year: 1919).*
Senftleben et al. The IKK/NF-KB Pathway; Critical Care Medicine, vol. 30, No. 1, pp. s18-s26. (Year: 2002).*
Salminen et al. Terpenoids: Natural Inhibitors of NF-KB Signaling With Anti-Inflammatory and Anticancer Potential; Cellular and Molecular Life Sciences, vol. 65, pp. 2979-2999. (Year: 2008).*
Ishii et al., "Suppression of the Progression of Diabetes and Nephopathy by Astaxanthin", Proceedings of the 45th Annual Meeting of the Japan Diabetes Society, Apr. 2002.
Muscaritoli et al., (Abstract Only) "Therapy of Muscle Wasting in Cancer: What is the Future", Curr. Opin. Nutri. Metab. Care, vol. 7, pp. 459-466. (2004).
Jackman, et al., "The Molecular Basis of Skeletal Muscle Atrophy", American Journal Physiol. Cell Physiol., vol. 287, pp. C834-C843. (2004).
"Collagen: The Fibrous Proteins of the Matrix," in Ladish et al. (ed.) Molecular Cell Biology (New York, W.H. Freeman, 2000 ed.), section 22.3.
Lee et al., "*Axtaxanthin Inhibits Nitric Oxide Production and Inflammatory Gene Expression by Suppressing IkB Kinase-dependent NF-1kB Activation*", Mol. Cells, 2003, 16(1), pp. 97-105.
Naito et al., "*Prevention of diabetic nephropathy by treatment with astaxanthin in diabetic db/db mice*", Bio Factors, 2004, 20, pp. 46-59.
Aoi et al., "*Astaxanthin Limits Exercise-Induced Skeletal and Cardiac Muscle Damage in Mice*", Antioxidants & Redox Signaling, 2003, 5(1), pp. 139-144.
Uchiyama et al., "*Astaxanthin protect β-cells against glucose toxicity in diabetic db/db mice*", Redox Report, 2002, 7(5), pp. 290-293.
Li et al., "*Alpha-tocopherol and astaxanthin decrease macrophage infiltration, apoptosis and vulnerability in atheroma of hyperlipidaemic rabbits*", 2004, Journal of Molecular and Cellular Cardiology, 37, pp. 969-978.
Guerin et al., "*Haematococcus astaxanthin: applications for human health and nutrition*", Trends in Biotechnology, 2003, 21, pp. 210-216.
Breithaupt, "*Identification and Quantifacation of Astaxanthin Esters in Shrimp (Pandalus borealis) and in a Microalga (Haematococcus pluvialis) by Liquid Chromatography-Mass Spectrometry Using Negative Ion Atmospheric Pressure Chemical Ionization*", J. Agric. Food Chem., 2004, 52, pp. 3870-3875.
World Health Organization website, International Statistical Classification of Diseases and Related Health Problems, 10th Revision, Version for 2005, http://apps.who.int/classifications/apps/icd/icd10online2005/fr-icd.htm, Sections VI, G56 and XIII, M62.5.
Barton et al., "Mechanisms and Strategies to Counter Muscle Atrophy," Journal of Geroniology: Medical Sciences, vol. 58A, No. 10, pp. 923-926 (2003).
Sandri et al., "Foxo Transcription Factors Induce the Atrophy-Related Ubiquitin Ligase Atrogin-1 and Cause Skeletal Muscle Atrophy," Cell, 117(3): pp. 399-412 (Apr. 2004).
Sandri M., "Signaling in Muscle Atrophy and Hypertrophy," Physiology, vol. 23, pp. 161-162 (Jun. 2008).
Nishikori, "Classical and Alternative NF-xB Activation Pathways and Their Roles in Lymphoid Malignancies", J. Clin. Hematopathol, vol. 45, No. 1, Aug. 2005, pp. 25-24.

* cited by examiner

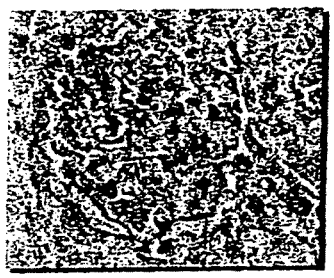  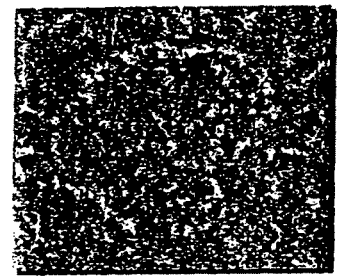
db/db     db/db(Ax)     db/m

REDUCING MUSCLE ATROPHY BY ADMINISTERING ASTAXANTHIN

CROSS-REFERENCE TO RELATED APPLICATIONS

This application is a continuation of U.S. application Ser. No. 12/155,914, filed Jun. 6, 2008, now abandoned, which is divisional of U.S. application Ser. No. 11/498,725, filed Aug. 4, 2006, now abandoned, which is a continuation of International Application No. PCT/JP2005/001718, filed on Feb. 4, 2005, which claims priority to Japanese Application No. JP 2004-028698, filed Feb. 4, 2004, all of which are hereby incorporated by reference in their entirety.

BACKGROUND OF THE INVENTION

Field of the Invention

The present invention relates to a gene expression regulating agent which comprises astaxanthin and/or its ester as an effective ingredient; and a food and drink having an effect of regulating gene expression comprising astaxanthin and/or its ester.

Description of the Related Art

In recent years, an attention has been paid to the relation between the oxidative damage induced by oxidized substances, and coronary heart disease, cancer, aging, or the like, especially, the relation with the deterioration of tissue and the inhibition of enzyme function or gene expression due to the oxidization of molecules within the living body. Inhibition of oxidative damage induced by free radicals may decrease the risk of such degenerative diseases. There are reports on the inhibition of the oxidization of molecules within the living body by natural or synthetic antioxidants.

In recent years, it has been found that astaxanthin, which is a kind of carotenoids as is β-carotene, has a strong antioxidant effect, 100 to 1,000 times as strong as vitamin E (α-tocopherol) and about 40 times as strong as β-carotene. The astaxanthin is a red dye and has long been eaten. It is widely distributed in nature, especially in the ocean and found in, for example, crustaceans such as shrimp and crab, fishes such as salmon and porgy, algae such as green alga *Haematococcus*, and yeasts such as red yeast *Phaffia*. The astaxanthin was used to be treated only as a dye; however, since the above-mentioned findings, astaxanthin is expected as a healthy food in to the industry.

Astaxanthin has other functional properties, and there are many reports including, for example, anti-inflammatory effect, anti-atherogenic effect, effect to improve ability to remember, effect to adjust diurnal rhythm, immunostimulatory effect, antistress effect, effect to improve muscle endurance, retina protective effect against light-induced damage, effect to improve regulatory function of eyes, effect to improve quality of sperm, and inhibition of induction of bladder cancer. In addition, as for the effect on the skin, effects to inhibit pigmentation, melanin production, and light aging are reported.

It has been reported that administration of astaxanthin into diabetic mice reduces blood glucose level and astaxanthin has an effect on the improvement of diabetic nephropathy (Naito Y. et al; Astaxanthin protects beta-cells against glucose toxicity in diabetic db/db mice. Redox Rep, 7(5), 290-3, 2002). In addition, Japanese Patent Application Laid-Open No. 2003-265136 describes that administration of astaxanthin into diabetic mice reduces the symptom of diabetic nephropathy and provides a food intake system based on the DNA testing of an individual organism.

However, regulation of gene expression by astaxanthin and/or its ester is not known.

SUMMARY OF THE INVENTION

The inventors of the present invention searched substances that regulate gene expression in order to solve above-mentioned problems. As a result, they have found that astaxanthin and/or its ester perform to regulate gene expression. The invention has been accomplished based on such findings, and provides a gene expression regulating agent which comprises astaxanthin and/or its ester as an effective ingredient; and a food and drink having an effect of regulating gene expression comprising astaxanthin or an ester thereof.

An object of the present invention is to provide a gene expression regulating agent which comprises astaxanthin and/or its ester as an effective ingredient; and a food and drink having an effect of regulating gene expression comprising astaxanthin or an ester thereof. The agent and the food and drink of the invention is useful for treating, improving, and preventing the disease caused by the promotion of gene expression and the disease caused by the suppression of gene expression by regulating abnormal gene expression.

In order to solve the above-mentioned problems, inventors of the present invention have investigated vigorously, and have found that astaxanthin and/or its ester has an effect of regulating gene expression. The invention is based on such findings.

Specifically, the invention includes (1) a method for regulating gene expression, including administering at least one of astaxanthin and an ester thereof as an effective ingredient, (2) a method for regulating cytokine-related gene expression, including administering at least one of astaxanthin and an ester thereof as an effective ingredient, (3) a method for regulating TGF-α-related gene expression, including administering at least one of astaxanthin and an ester thereof as an effective ingredient, (4) a method for regulating collagen-related gene expression, including administering at least one of astaxanthin and an ester thereof as an effective ingredient, (5) a method for regulating the expression of gene related to the increase and decrease of muscle cell and bone cell, including administering at least one of astaxanthin and an ester thereof as an effective ingredient, (6) the method for regulating gene expression according to any one of (1) to (5), wherein the at least one of astaxanthin and an ester thereof is administered as an effective ingredient in the form of a food or a drink, and (7) a method for using at least one of astaxanthin and an ester thereof in order to produce the gene expression regulating agent of any one of (1) to (6).

BRIEF DESCRIPTION OF THE DRAWING

FIG. 1 is a photomicrograph of the renal glomerulus of Example 1. db/db, db/db(Ax), and db/m are renal glomeruli of db/db mouse, astaxanthin-administered mouse, and db/m mouse, respectively.

DESCRIPTION OF THE PREFERRED EMBODIMENTS

Hereinafter, the invention will be described in detail. In the invention, "effect of regulating gene expression" refers to the effect to regulate abnormal gene expression, which causes various kinds of diseases due to a variety of factors, to the gene expression in a normal condition, that is, when gene expression is promoted abnormally, gene expression is moderated, and when gene expression is moderated abnormally, gene expression is promoted, thereby regulating gene expression in a proper way.

The gene to be regulated may be any type without limitation; examples thereof include genes related to oxidation, cytokines, collagen, TGF, and the increase and decrease of muscle cell and bone cell.

Specific examples thereof include genes related to the production of enzymes or factors pertaining to oxidation such as peroxyredoxin, catalase, dehydrogenase, and superoxidase dismutase; genes related to the production of enzymes or factors pertaining to cytokine such as septin, fibrosin, granulin, RING finger protein, protein phosphatase, secreted phosphoprotein, FMS-like tyrosine kinase, erythropoietin receptor, colony stimulating factor, interleukin, and fibrosin; genes related to the production of enzymes or factors pertaining to collagen such as insulin-like growth factor receptor, macrophage scavenger receptors, collagen type XXV, procollagen type IV, C1q and tumor necrosis factor related protein, C1q-related factor, and matrix metalloproteinase; genes related to the production of enzymes or factors pertaining to TGF such as FK506 binding protein, catenin beta, MAD homolog, TGF beta induced transcript, selected phosphoprotein; and genes related to the production of enzymes or factors pertaining to the increase and decrease of muscle fiber or muscle cell and bone cell such as phosphatidyl inositol 3 kinase, lysosome protease, cytoplasmic protease, RT1, and neuronatin.

The gene expression regulating agent of the invention into which astaxanthin and/or its ester is compounded and the food and drink of the invention into which astaxanthin and/or its ester is compounded can treat, improve, and/or prevent the disease caused by the abnormality of gene expression.

The term "astaxanthin" in the invention means those derived from natural sources or synthetic ones. Examples of those derived from natural sources include those derived from crustacean shells such as a shrimp, krill, and crab; skis or eggs of various kinds of fish and shellfish; algae such as green alga *Haematococcus*, yeasts such as red yeast *Phaffia*, marine bacteria, seed plants such as an adonis and buttercup. Natural extracts and chemically-synthesized compounds are easily available.

Astaxanthin can be obtained by culturing, for example, red yeast *Phaffia*, green alga *Haematococcus*, or marine bacteria in an appropriate culture according to the method known in the art. Green alga *Haematococcus* is most suitable in terms of easy culturing and extraction and in that resulting products contain astaxanthin in highest concentration and productivity is high. For the culturing method to obtain products containing a high amount of astaxanthin from *Haematococcus* green algae, closed type culturing method, which prevents the mixture and propagation of heterologous microorganisms and allows fewer impurities to be mixed, is preferable. For example, following methods are suitable: a method in which culturing is performed using a culture apparatus that comprises a partially open type culture device of a domed shape, a conical shape, or a cylindrical shape; and a gas discharge device disposed so as to be movable in the culture device (International Publication No. WO 99/50384); a method in which culturing is performed by irradiating inside with light from a light source arranged inside a closed type culture device and; and a method in which culturing is performed in a tabular fermenter.

Various methods are known for extraction or purification from the culture or the crustacean. Astaxanthin and esters thereof are lipid soluble substances. Thus, for example, astaxanthin-containing components can be extracted from natural sources containing astaxanthin with a lipid soluble organic solvent such as acetone, alcohol, ethyl acetate, benzene, and chloroform. In addition, supercritical extraction can also be performed using carbon dioxide and water. After the extraction, the concentrated mixture of monoester form of astaxanthin and diester form of astaxanthin can be obtained by removing the solvent according to a usual method. The resulting concentrate can be further purified with a separation column or lipase degradation, if necessary.

Alternatively, astaxanthin can be extracted by drying *Haematococcus* alga cultured in the domed shape or closed type culture device, extracting with acetone after grinding, or simultaneously performing grinding and extraction in acetone, and then removing acetone. This process is advantageous in that the resulting extracts contain less impurities, i.e., fewer substances inhibiting the effect of regulating gene expression of the invention, and thus contains more astaxanthin and triglyceride with high purity.

Astaxanthin can be used in such forms as extracts of astaxanthin to be obtained by the above-mentioned method and powders or solutions containing the extracts, or dried products of e.g. red yeast *Phaffia*, green alga *Haematococcus*, or marine bacteria and crushed products thereof.

Astaxanthin is 3,3'-dihydroxy-β,β-carotene-4,4'-dione and has stereoisomers. Specifically, three stereoisomers (3R, 3'R)-astaxanthin, (3R,3'S)-astaxanthin, and (3S,3'S)-astaxanthin are known, all of which can be used in the invention.

In the description of the invention, "astaxanthin" includes astaxanthin and/or its ester unless otherwise described. Further, esters of astaxanthin include monoester form and/or diester form.

It is known that astaxanthin has not been observed having any mutagenicity and is a highly safe compound. It is widely used as a food additive (Takahashi Jiro et al; Toxicity test of *Haematococcus* alga astaxanthin-Ames test, rat single-dose toxicity test, rat 90-day repeat dose oral toxicity test-, Rinsho Iyaku, 20: 867-881, 2004).

At least one of free form, monoester form, and diester form of astaxanthin can be used for the gene expression regulating agent of the invention which comprises astaxanthin and/or its ester as an effective ingredient. The diester form is physically more stable than the free form and monoester form and hard to be subjected to oxidative decomposition, because its two hydroxy groups are protected by ester bonds. However, when it is taken into the living body, it is considered to be hydrolyzed quickly into free astaxanthin by in vivo enzyme to exert its effect.

Monoesters of astaxanthin include lower or higher saturated fatty acid esters, or lower or higher unsaturated fatty acid esters. Specific examples of the lower or higher saturated fatty acid, or lower or higher unsaturated fatty acid include acetic acid, lauric acid, myristic acid, pentadecanoic acid, palmitic acid, palmitoleic acid, heptadecanoic acid, elaidic acid, ricinoleic acid, petroselinic acid, vaccenic acid, eleostearic acid, punicinic acid, licanoic acid, palynalic acid, gadolic acid, 5-eicosenoic acid, 5-docosenoic acid, cetolic acid, ercinoic acid, 5,13-docosadienoic acid, selacholic acid, decenoic acid, stering acid, dodecenoic acid, oleic acid, stearic acid, eicosapentaenoic acid, docosahexaenoic acid, linoleic acid, linolenic acid, and arachidonic acid. Diesters of astaxanthin include diesters of the same or different fatty acids selected from the group consisting of the above-mentioned fatty acids.

Further, examples of monoester of astaxanthin include monoesters of an amino acid such as glycine and alanine; a mono- or poly-carboxylic acid such as acetic acid and citric acid; an inorganic acid such as phosphoric acid and sulfuric acid; a sugar such as glucoside; a sugar fatty acid such as glycoglycero-fatty acid and sphingoglyco-fatty acid; a fatty acid such as glycero-fatty acid; glycerophosphoric acid; and the like. When it is possible, salts of the above-mentioned monoesters are also included.

Diesters of astaxanthin include diesters composed of the same or different acids selected from the group consisting of above-mentioned lower saturated fatty acids, higher saturated fatty acids, lower unsaturated fatty acids, higher unsaturated fatty acids, amino acids, mono- or poly-carboxylic acids, inorganic acids, sugars, sugar fatty acids, fatty acids, and glycerophosphoric acids. When it is possible, salts of the above-mentioned diesters are also included. Examples of diesters of glycerophosphoric acid include saturated fatty acid esters of glycerophosphoric acid and esters of glycerophosphoric acid containing fatty acids selected from higher unsaturated fatty acids, unsaturated fatty acids, or saturated fatty acids.

The gene expression regulating agent of the invention is useful for treating, improving and/or preventing the increase of enzymes and factors caused by abnormal expression and the decrease or deficiency of enzymes and factors caused by abnormal suppression. By regulating gene expression, production and/or inhibition of enzymes and factors can be regulated. Thus, the gene expression regulating agent of the invention has an effect on treating, improving and/or preventing diseases that are said to be developed due to the abnormal gene expression, for example, arteriosclerosis, hypertension, diabetes, cancer, hyperlipemia, rheumatism, gout, stroke, ischemic heart disease, pulmonary emphysema, gastric ulcer, pancreatitis, nephritis, cataract, Alzheimer's disease, allergic disease, aging, neuropathy which is a complication of diabetes, retinopathy, diseases related to nephropathy and hemopathy. In case of neuropathy, the agent of the invention has an effect on treating, improving and/or preventing sudden hearing loss, abnormality in eyes or in face (paralysis and pain), orthostatic hypotension, dyshidrosis, diarrhea and constipation (digestive symptom), urinary disturbance, pain of extremity, sensory abnormality, atrophy of muscles, and gangrene. In case of retinopathy, the agent of the invention has an effect on macular degeneration, glaucoma, cataract, simple retinopathy, preproliferative retinopathy, and proliferative retinopathy. In case of hemopathy, the agent of the invention has an effect on treating, improving and/or preventing cerebral infarction and myocardial infarction.

The gene expression regulating agent of the invention which comprises astaxanthin and/or its ester as an effective ingredient can be administered orally or non-orally. The agent can be administered orally in a solid form such as a tablet, orally disintegrating tablet, capsule, granule, fine granule, or in a liquid form such as a syrup and suspension. The agent can be administered non-orally in a form such as an injection, eyedrops, nasal drops, adhesive preparation, ointment, and suppository.

The gene expression regulating agent of the invention which comprises astaxanthin and/or its ester as an effective ingredient may comprise various kinds of additives that are used in the production of general formulation in an appropriate amount. Examples of such additives include excipients, binders, acidulants, foaming agents, artificial sweeteners, flavors, lubricants, colorants, stabilizers, pH adjusters, surfactants, and the like. Examples of excipient include starches such as cornstarch, potato starch, wheat starch, rice starch, partly pregelatinized starch, pregelatinized starch, and porous starch; sugars such as lactose, fructose, and glucose; sugar alcohols such as mannitol, xylitol, erythritol, sorbitol, and maltitol; and inorganic compounds such as magnesium aluminometasilicate, hydrotalcite, anhydrous calcium phosphate, precipitated calcium carbonate, calcium silicate, and light anhydrous silicic acid. Examples of binder include hydroxypropyl cellulose, hydroxypropylmethyl cellulose, polyvinylpyrrolidone, gum arabic powder, gelatin, and pullulan. Examples of disintegrant include starch, agar, carmellose calcium, sodium carboxymethyl starch, croscarmellose sodium, crospovidone, and crystalline cellulose. Examples of acidulant include citric acid, tartaric acid, malic acid and ascorbic acid. Examples of foaming agent include sodium hydrogencarbonate and sodium carbonate. Examples of sweetener include saccharine sodium, dipotassium glycyrrhizinate, aspartame, stevia, and thaumatin. Examples of flavor include lemon oil, orange oil, and menthol. Examples of lubricant include magnesium stearate, sucrose esters of fatty acids, polyethylene glycol; talc, stearic acid, and sodium stearyl fumarate. Examples of colorant include food colors such as Food Yellow No. 5, Food Red No. 2, and Food Blue No. 2, food lake colors, and diiron trioxide. Examples of stabilizer include sodium edentate, tocopherol, and cyclodextrins. Examples of pH adjuster include citrate, to phosphate, carbonate, tartrate, fumarate, acetate, and amino acid salt. Examples of surfactant include polysorbate 80, methylcellulose, hydroxyethylcellulose, sodium carboxymethylcellulose, polyoxyethylene sorbitan monolaurate, gum arabic, and powdered tragacanth. Astaxanthin can be compounded as a powder or granule after wet granulation.

Liquid forms such as a syrup, drink, suspension, eyedrops, and injection can be obtained by preparing an effective ingredient in the presence of a pH adjuster, buffer, resolvent, suspension, tonicity agent, stabilizer, preservative, etc. on as-needed basis according to a usual method. Examples of suspension include polysorbate 80, methylcellulose, hydroxyethyl cellulose, sodium carboxymethyl cellulose, polyoxyethylene sorbitan monolaurate, gum arabic, and powdered tragacanth. Examples of resolvent include polysorbate 80, hydrogenated polyoxyethylene castor oil, nicotinic acid amide, polyoxyethylene sorbitan monolaurate, macrogol, and castor oil fatty acid ethyl ester. Examples of stabilizer include sodium sulfite and sodium metasulfite. Examples of preservative include methyl p-hydroxybenzoate, ethyl p-hydroxybenzoate, sorbic acid, phenol, cresol, and chlorocresol.

In order to enhance the effect of regulating gene expression according to the invention, substances having antioxidant capacity may be added. Antioxidant is thought to enhance the effect of astaxanthin, for example, by inhibiting the oxidation of astaxanthin in the gene expression regulating agent of the invention, or by inhibiting the oxidation of astaxanthin in the living body. The antioxidant is not particularly limited and those having an antioxidant effect are applicable. The antioxidant can be selected from the group consisting of vitamin As such as retinol and 3,4-didehydroretinol; vitamin B; vitamin Cs such as D-ascorbic acid and L-ascorbic acid; vitamin Es such as tocopherol, tocotrienol, vitamin E acetate, vitamin E succinate, and vitamin E phosphate; carotenoids such as β-carotene and lutein, and pharmaceutically allowable salts of these; coenzyme Q flavonoid, tannin, ellagic acid, polyphenols, nucleic acids, herb medicines, marine algae, and inorganic substances; and mixtures thereof. These may be used singly or in combination. In addition, the same effect can be achieved by compounding a fruit, or algae, fungi, or the like containing these into the agent of the invention.

For an external preparation for skin in form, in addition to the above components, components for use in an external preparation for skin such as usual cosmetics and medicines, for example, a whitening agent, humectant, antioxidant, oily component, ultraviolet absorber, surfactant, thickener, alcohol, powder component, coloring material, aqueous component, water, skin nutritional supplement, or the like may be appropriately compounded on as-needed basis.

The amount of astaxanthin or its ester for use in the gene expression regulating agent of the invention is a dosage of 0.5 mg to 100 mg, preferably 1 mg to 20 mg in terms of free astaxanthin per day for adults, administered orally or non-orally. The dosage may vary depending on the age, body weight or grade of symptoms of a patient to be administered, or administration form. The pharmaceutical agent of the invention may comprise astaxanthin in an amount of 0.01% by weight to 99.9% by weight, preferably 0.1% by weight to 90% by weight.

The invention encompasses a food and drink having an effect of regulating gene expression comprising astaxanthin or its ester.

Examples of the form of the food and drink include common foods such as margarine, butter, butter sauce, cheese, raw cream, shortening, lard, ice cream, yogurt, diary products, meat sauce products, fish products, pickles, fried potato, potato chips, snack food, thin slices of dried rice cake, popcorn, seasoned powder for sprinkling over rice, chewing gum, chocolate, pudding, jelly, gumi-candy, candy, drops, caramel, bread, sponge cake, cake, doughnut, biscuit, cookie, cracker, macaroni, pasta, Chinese noodles in soup, buckwheat noodles, wheat-flour noodles, salad oils, instant soup, dressing, egg, mayonnaise, miso, or carbonated or non-carbonated drinks such as fruit drinks, refreshing drinks, sports drinks, non-alcoholic drinks such as tea, coffee, and cocoa, or alcoholic drinks such as liqueur, and medicinal alcoholic beverages.

The food and drink of the invention can be produced by compounding astaxanthin and/or its ester with raw materials of common food and processing according to a usual method. The amount of astaxanthin and/or its ester to be compounded is different depending on the form of food and is not particularly limited. In general, the amount is 0.00001% by weight to 10% by weight, preferably 0.0001% by weight to 5% by weight, and the astaxanthin and/or its ester is adjusted so that necessary amount of astaxanthin and/or its ester to exert the preventing or improving effect is contained. The amount of astaxanthin and/or its ester to be used can be selected appropriately depending on the kind of food and drink by is those skilled in the art, and the amount is an intake of 0.5 mg to 100 mg, preferably 1 mg to 20 mg per day for adults.

When the food and drink of the invention are used as nutritional and supplemental foods or functional foods, their forms may be the same as the above-mentioned pharmaceutical preparation. There may also be used in combination milk protein, soybean protein, or egg albumin protein, or the decomposition product thereof, oligopeptide of egg white, soybean hydrolyzate, or a mixture of them with a single amino acid. The food and drink may be in a processed form, such as natural liquid foods, semi-digested nutritional foods and nutritional foods, drinks, capsules or enteral nutrients, etc. combined with sugars, fats, trace elements, vitamins, emulsions, flavors, or the like. For the drink form, the material can be combined with the drink as nutritional additives such as amino acids, vitamins, and minerals and sweeteners, spices, flavors, pigments, etc., in order to keep a nutrient balance or to impart a good taste when ingested. The form of the food and drink of the invention is not limited to these.

Hereinafter, Examples will be described to explain the invention in more detail, but it will be obvious that the invention is not restricted to these Examples.

Example 1

[Onset of Diabetic Complication]

Type II diabetic female db/db mice and non-diabetic db/m were purchased from Clea Japan, Inc. Mice were bred under the conditions with a 12 hours light-dark cycle at a temperature of 21° C. to 25° C. For acclimation, mice were fed CE-2 (Clea Japan, Inc.) with free access to water for one week. The mice were divided into three groups each consisting of 8 mice (non-diabetic db/m, diabetic db/db, and astaxanthin-administered db/db) and each group was bred with feed ad libitum. Mice in astaxanthin-administered group were fed a diet in which 0.02% astaxanthin in terms of free astaxanthin was compounded with CE-2. Each group was bred for 12 weeks, and body weight, blood glucose levels, 8-OHdG levels in urine, albumin levels in urine, and kidney histopathology, were measured. Astaxanthin used here was AstaReal (registered trademark, Fuji Chemical Industry Co., Ltd.) 50F, which is oil composed of astaxanthin fatty acid ester and triglycerides and contains 5% astaxanthin in terms of free astaxanthin.

TABLE 1

Change of albumin level in urine and
8-OHdG level in urine at the start

| Group | Albumin level in urine (mg/dl) | 8-OHdG level in urine (mg/dl) |
|---|---|---|
| db/db | 46.9 ± 0.6 | 421.5 ± 22.5 |
| db/db (Ax) | 46.2 ± 1.5 | 325.2 ± 38.5 |
| db/m | 30.2 ± 1.2 | 119.4 ± 3.6 |

Each value represents standard deviation * $p<0.01$ administered group vs control (t-test)

db/db, db/db (Ax), db/m are db/db mice, astaxanthin-administered db/db mice, and db/m mice, respectively.

TABLE 2

Change of albumin level in urine and
8-OHdG level in urine at the end

| Group | Albumin level in urine (mg/dl) | 8-OHdG level in urine (mg/dl) |
|---|---|---|
| db/db | 236.2 ± 173.5 | 335.8 ± 67.9 |
| db/db (Ax) | 77.8 ± 44.6 | 160.5 ± 43.5 |
| db/m | 75.5 ± 43.9 | 75.0 ± 15.1 |

Each value represents standard deviation * $p<0.01$ administered group vs control (t-test)

Tables 1 and 2 show the effect of astaxanthin on the blood glucose levels, albumin levels in urine, and 8-OHdG levels in urine of diabetic mice.

These results indicate that astaxanthin in diabetes reduces blood glucose levels, albumin levels in urine, and 8-OHdG levels in urine and thus has an effect on diabetes and diabetic nephropathy.

The kidney was removed from each of db/db, db/db(Ax), and db/m mice, thinly sliced, and then the glomerulus was observed with a microscope. The glomerular mesangium of db/db mice was enlarged, however, the enlargement of glomerular mesangium was apparently moderated in case of astaxanthin-administered db/db(Ax). FIG. 1 is a photomicrograph of glomerulus. It was revealed that since astaxanthin moderated the lesion of renal glomerulus, the increase of albumin levels in urine and 8-OHdG levels in urine in diabetic to nephropathy was reduced.

[Measurement of Degree of Gene Expression]

After the period of test breeding, kidney was removed and frozen at −80° C. Using an LM200 system (Olympus Corporation), the renal glomerulus was cut from kidney of mice while keeping low temperature. tRNA of renal glomerulus was extracted using tRNA extraction regent "Isogen" (produced by Nippon Gene Co., Ltd.), and then preparation of cRNA and hybridization were performed according to the Affymetrix GeneChip Eukaryotic Small Sample Target Labeling Assay Ver. II.

(1) Synthesis of first strand cDNA: 1 μL of total RNA solution and 1 of 5 μM T7-Oligo(dT) primer were mixed, heated at 70° C. for 6 minutes, and then cooled at 4° C. for 2 minutes. 3 μL of RT_Premix_1 (1.5 μL DEPC-treated water, 4 μL 5× First strand Buffer, 2 μL DTT (0.1 M), 1.5 μL dNTP Mix (10 mM), 1 μL RNase inhibitor (40 U/μL), and 2 μL Super-Script II (200 U/μL)) was added and reverse transcribed at 42° C. for 1 hour. The sample was heated at 70° C. for 10 minutes to inactivate Super Script II, and then cooled to 4° C.

(2) Synthesis of second strand cDNA: 32.5 μl of SS_Premix_1 (91 μL DEPC-treated water, 30 μL 5× Second Strand Buffer, 3 μL dNTP (10 mM), 1 μL E. coli DNA ligase (10 U/μL); 4 μL E. coli DNA polymerase (10 U/μL), and 1 μL RNase H (2 U/μL)) was added to the first strand cDNA solution and allowed to react for 2 hours at 16° C.

(3) To the resulting cDNA, was added 1 μL T4 DNA polymerase (5 U/μl) and allowed to react for 10 minutes at 16° C., and purified by ethanol precipitation.

(4) In vitro transcription: To the dried double-stranded cDNA pellet, was added 10 μL of reagents (4 μL DEPC-treated water, 4 μL premixed NTPs, 1 μL 10× reaction buffer, and 1 μL 10× enzyme mix), and allowed to react at 37° C. in a water bath for 6 hours.

(5) First cycle cRNA was purified using the RNeasy Mini Kit in accordance with the protocol in the handbook (QIAGEN).

(6) Subsequently, for the amplification and labeling, the cRNA sample was mixed with random primers (0.2 μg/μL), treated at 70° C. for 10 minutes, cooled on ice for 2 minutes, 5 μL of RT_Premix_2 (5× First Strand Buffer, DTT (0.1 M), dNTP mix (10 mM), RNase inhibitor (40 U/μL), and Super-Script II (200 U/μL) was added, and allowed to react at 42° C. for 1 hour.

(7) Next, Second Sstrand cDNA synthesis was carried out by adding 5 μM T7-Oligo(dT) promoter treating at 70° C. for 6 minutes, cooling at 4° C., and adding 62 μL of SS_Premix_2 (43 μL it DEPC-treated water, 15 μL 5× Second Strand Buffer, 1.5 μL dNTP mix (10 mM), and 2 μL E. coli DNA polymerase (10 U/μL)).

(8) To the resulting cDNA, was treated added 1 μL of T4 DNA polymerase (5 U/μL), allowed to react at 16° C. for 10 minutes, and purified by ethanol precipitation.

(9) To perform in vitro transcription and labeling with the ENZO BioArray High Yield RNA Transcript Labeling Kit, 40 μL of reagents (22 μL DEPC-treated solution, 4 μL 10×HY reaction buffer, 4 μL 10× biotin-labeled ribonucleotides, 4 μL 10×DTT, 4 μL 10× RNase to inhibition mix, and 2 μL 20× T7 RNA polymerase) were added, and allowed to react at 37° C. for 4 hours.

(10) Labeled cRNA target was purified with RNeasy columns.

(11) The fragmentation and hybridization were performed according to "GeneChip Expression Analysis Technical Manual".

The prepared labeled cRNA was hybridized to a GeneChip "mouse Expression Set 430A, representing a total of 22,690 mouse transcripts" (Affymetrix). For data analysis, the GeneChip Analysis Suite Ver. 5.1 (Affymetrix) was used. All microarrays were scaled to a target intensity of 1000 and were compared with background, noise, and overall staining intensity. Differentially expressed transcripts were identified by algorithms of the software y Affymetrix.

TABLE 3

Oxidative stress-related gene expression intensity ratio

| Accession No. | db/db: db/m | db/db(Ax): db/db | db/db(Ax): db/m | Descriptions |
|---|---|---|---|---|
| 1424111_at | 13.00 | 0.87 | 11.31 | insulin like growth factor 2 receptor |
| 1448061_at | 5.28 | 0.25 | 1.32 | macrophage scavenger receptor 1 |
| 1438655_a_at | 4.59 | 0.19 | 0.87 | collagen, type XXV, alpha 1 |
| 1425476_at | 4.00 | 0.50 | 2.00 | procollagen, type IV, alpha 5 |
| 1424762_at | 0.62 | 2.00 | 1.23 | C1q and tumor necrosis factor related protein 5 |
| 1422777_at | 0.54 | 1.32 | 0.71 | C1q related factor |
| 1449366_at | 0.31 | 2.00 | 0.62 | matrix metalloproteinase 8 |

* Accession No. is the site number of "mouse Expression Set 430A" to which probes are attached, db/db:db/m, db/db(Ax):db/db, and db/db(Ax):db/m represent the gene expression intensity ratio between db/db mice and db/m mice, the gene expression intensity ratio between the astaxanthin-administered db/db mice and db/db mice, and the gene expression intensity ratio between the astaxanthin-administered db/db mice and db/m mice, respectively.

In the "Descriptions", factors, with which the attached probe is associated, are shown. Tables 4 to 6 listed below are described in the same way.

TABLE 4

Cytokine-related gene expression relative ratio

| Accession No. | db/db: db/m | db/db(Ax): db/db | db/db(Ax): db/m | Descriptions |
|---|---|---|---|---|
| 1434099_at | 78.79 | 0.87 | 68.59 | caspase 7 |
| 1420811_a_at | 32.00 | 0.38 | 12.13 | catenin beta |
| 1422486_a_at | 27.86 | 1.00 | 27.86 | MAD homolog 4 (Dorosophia) |
| 1448184_at | 9.85 | 0.66 | 6.50 | FK506 binding protein 1a |
| 1454971_x_at | 5.66 | 0.57 | 3.25 | transforming growth factor beta 1 induced transcript 4 |
| 1449254_at | 4.92 | 0.13 | 0.66 | secreted posphoprotein 1 |
| 1425742_a_at | 4.29 | 0.33 | 1.41 | transforming growth factor beta 1 induced transcript 4 |

TABLE 5

Cytokine-related gene expression relative ratio

| Accession No. | db/db: db/m | db/db(Ax): db/db | db/db(Ax): db/m | Descriptions |
|---|---|---|---|---|
| 1436691_x_at | 64.00 | 0.14 | 9.19 | peroxiredoxin 1 |
| 1416430_at | 25.99 | 0.33 | 8.57 | catalase |
| 1419821_s_at | 21.11 | 0.33 | 6.96 | isocitrate dehydrogenase 1 (NADP+), soluble |
| 1448184_at | 17.15 | 0.23 | 4.00 | superoxide dismutase 1, soluble |
| 1448733_at | 10.56 | 0.76 | 8.00 | Blymphoma Mo-MLV insertion region 1 |

TABLE 6

Cytokine-related gene expression relative ratio

| Accession No. | db/db: db/m | db/db(Ax): db/db | db/db(Ax): db/m | Descriptions |
|---|---|---|---|---|
| 1454610_at | 48.5 | 0.76 | 36.76 | septin 7 |
| 1433816_at | 25.99 | 0.31 | 8 | fibrosin 1 |
| 1438629_x_at | 16 | 0.19 | 3.03 | granulin |
| 1449036_at | 16 | 0.1 | 1.62 | ring finger protein 128 |
| 1423344_at | 0.31 | 2.30 | 0.71 | erythropoietin receptor |

It is found that excessively expressed genes of db/db mice where abnormal gene expression has taken place are moderated, whereas the expression of genes with decreased expression are improved.

Example 2

[Muscle Atrophy Test]

9-week-old Wistar male rats were bred each being fed a normal diet for breeding and water ad libitum under the conditions with a 12 hours light-dark cycle at a temperature of 21° C. to 25° C. and were accustomed to the environment in advance. The rats were divided into two groups of 10 rats per group, and each group was bred with a normal diet (control group) or a diet to which astaxanthin was added (Ax group) fed ad libitum. The diet to which astaxanthin was added was prepared by mixing free astaxanthin at 0.02%. At one week after the start of ingestion of astaxanthin-added diet, the sciatic nerve of the left leg was cut and muscle of the left lower extremity was inactivated. After breeding for further two weeks, rats were killed, triceps surae (soleus muscle, gastrocnemius, and plantaris) were extracted from left leg (limb in which nerves were removed) and right leg (control limb), respectively, and the wet weight of the gastrocnemius was measured. The atrophy rate was calculated using the difference of the wet weight of the gastrocnemius of left lower limb to the wet weight of the gastrocnemius of right lower limb with respect to each group Table 7. By the above-mentioned measurement of degree of gene expression, global measurement of mRNA expression was performed using GENEchip (Affymetrix) with respect to the gastrocnemius of right and left legs of each of the control group and astaxanthin-administered group Table 8.

TABLE 7

Weight of gastrocnemius and change of atrophy rate

| | | Control group | Ax group |
|---|---|---|---|
| Body weight (g) | | 343.8 | 338.7 |
| Gastrocnemius | Right leg weight (mg) | 5.05 ± 0.32 | 4.94 ± 0.27 |
| | Light leg weight (mg) | 2.84 ± 0.28 | 3.08 ± 0.10 |
| | Atrophy rate (%) | 43.8 | 37.7 |

The Ax group had a smaller value of atrophy rate compared with the control group, indicating that Ax has an effect to moderate muscle atrophy. The risk rate was 5% or less and significant results were obtained.

TABLE 8

Gene expression related to increase and decrease of muscle cell and bone cell (increase of expression)

| Acccession No. | ac/nc | ad/nd | nd | nc | ad | ac | Descriptions |
|---|---|---|---|---|---|---|---|
| 1369999_a_at | 0.79 | 0.61 | 1043.2 | 135 | 640.7 | 106.4 | neuronatin |
| 1377334_at | 1.60 | 0.51 | 615.4 | 137.6 | 312 | 220.5 | RT1 class II, locus Ba |

TABLE 8-continued

Gene expression related to increase and decrease of muscle
cell and bone cell (increase of expression)

| Acccession No. | ac/nc | ad/nd | nd | nc | ad | ac | Descriptions |
|---|---|---|---|---|---|---|---|
| 1387172_a_at | 1.06 | 0.57 | 1179 | 452.6 | 677.8 | 479.9 | transforming growth factor, beta 2 |
| 1387353_at | 0.83 | 0.67 | 1564 | 862.6 | 1042.6 | 715.4 | murine thymoma viral (v-akt) oncogene homolog 2 |

* Accession No. is the site number of "mouse Expression Set 430A" to which probes are attached, nd, nc, ad, and ac are luminescence intensities of the site, to which probes are attached, of the genes in gastrocnemius in left leg (limb in which nerves were removed) of control group, in gastrocnemius in right leg (control) of control group, in gastrocnemius in left leg (limb in which nerves were removed) of astaxanthin-administered group, and in gastrocnemius in right leg (control) of astaxanthin-administered group, respectively. ad/nc and ad/nd represent the gene expression intensity ratio of the gene in the gastrocnemius of the left leg (limb in which nerves were removed) of astaxanthin-administered group relative to the gene in the gastrocnemius of the right leg (control) of control group, and the gene expression intensity ratio of the gastrocnemius of the left leg (limb in which nerves were removed) of astaxanthin-administered group relative to the gastrocnemius of the left leg (limb in which nerves were removed) of control group, respectively. In the "Descriptions", factors, with which the attached probe is associated, are shown.

Table 9 is described in the same way.

It is found that the administration of astaxanthin moderates the increase of expression of muscle atrophy-related genes with increased expression.

TABLE 9

Gene expression related to increase and decrease of muscle
cell and bone cell (suppression of expression)

| Acccession No. | ac/nc | ad/nd | nd | nc | ad | ac | Descriptions |
|---|---|---|---|---|---|---|---|
| 1398469_at | 1.09 | 1.90 | 175.1 | 479.2 | 333.1 | 523.6 | Protein phosphatase 3, catalytic subunit gamma isoform |
| 1369098_at | 1.00 | 1.49 | 213.1 | 501.2 | 318 | 500.5 | very low density lipoprotein receptor |
| 1369161_at | 1.34 | 1.41 | 217.3 | 503.5 | 306.9 | 677.1 | ATP-binding cassette, sub-family B (MDR/TAP), member |

It is found that the administration of astaxanthin increases the expression of muscle atrophy-related genes with suppressed expression.

[Preparation Example 1] Tablet

The ingredients shown below were uniformly mixed in the following compositional ratio (% by weight) to make tablets, each being 180 mg.

| Astaxanthin | 5% |
| Lactose | 75% |
| Heavy magnesium oxide | 20% |

[Preparation Example 2] Capsule

*Haematococcus* extracted oil (containing 10% by weight of astaxanthin) was filled in a soft capsule film consisting of the following components according to a usual method to prepare soft capsules, each being 100 mg.

| Gelatin | 70% |
| Glycerin | 23% |
| Propyl p-hydroxybenzoate | 0.5% |
| Water | proper quantity |
| Total | 100% |

INDUSTRIAL APPLICABILITY

The invention revealed that astaxanthin has an effect of regulating gene expression and makes gene expression in a normal condition. Namely, the gene expression regulating agent of the invention is useful as the gene expression regulating agent which comprises astaxanthin or its ester as an effective ingredient.

What is claimed is:

1. A method for reducing muscle atrophy in limbs in a subject having muscle atrophy due to muscle inactivation caused by nerve injury, comprising administering to the subject at least one of the group consisting of isolated astaxanthin and an ester thereof as an effective ingredient, thereby increasing muscle weight.

2. The method according to claim 1, wherein the at least one of the group consisting of astaxanthin and an ester thereof is administered as an effective ingredient in the form of a food or a drink.

3. The method of claim 1, wherein the administration is oral.

4. The method of claim 1, wherein reducing muscle atrophy comprises improving gene expression.

5. The method of claim 1, wherein the nerve injury is due to denervation.

6. The method of claim 5, wherein the denervation is due to severing of the nerve.

7. The method of claim 5, wherein the denervation is due to cutting the nerve.

* * * * *

UNITED STATES PATENT AND TRADEMARK OFFICE
CERTIFICATE OF CORRECTION

PATENT NO. : 10,828,269 B2
APPLICATION NO. : 14/526880
DATED : November 10, 2020
INVENTOR(S) : Naito et al.

It is certified that error appears in the above-identified patent and that said Letters Patent is hereby corrected as shown below:

In the Specification

Column 1, Lines 7-14 is corrected to read as follows:
-- This application is a continuation of U.S. Application No. 12/155,915, filed June 11, 2008, which is a divisional of U.S. Application No. 11/498,725, filed August 4, 2006, which is a continuation of International Application No. PCT/JP2005/001718, filed on February 4, 2005, which claims priority to Japanese Application No. JP 2004-028698, filed February 4, 2004, all of which are hereby incorporated by reference in their entirety. --

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*